(12) United States Patent
Yi et al.

(10) Patent No.: US 10,113,957 B1
(45) Date of Patent: Oct. 30, 2018

(54) NON-DISPERSIVE INFRARED CARBON DIOXIDE GAS SENSOR WITH DEPOSITED HYDROPHOBIC THIN FILM

(71) Applicants: KOREA NATIONAL UNIVERSITY OF TRANSPORTATION Industry-Academic Cooperation Foundation, Chungju-si, Chungcheongbuk-do (KR); HUMAS. CO.LTD, Daejeon (KR)

(72) Inventors: SeungHwan Yi, Chungju-si (KR); Keun Heon Lee, Daejeon (KR); Hyeong-Gee Yeo, Bucheon-si (KR); Jin Ho Kim, Incheon (KR)

(73) Assignees: KOREA NATIONAL UNIVERSITY OF TRANSPORTATION; Industry-Academic Cooperation Foundation, Chungju-si (KR); HUMAS. CO.LTD, Daejeon (KR)

( * ) Notice: Subject to any disclaimer, the term of this patent is extended or adjusted under 35 U.S.C. 154(b) by 0 days.

(21) Appl. No.: 15/834,816

(22) Filed: Dec. 7, 2017

(30) Foreign Application Priority Data

Jun. 29, 2017 (KR) .................. 10-2017-0082522

(51) Int. Cl.
  *G01N 21/3518* (2014.01)
  *G01N 21/47* (2006.01)
  *G01N 33/00* (2006.01)

(52) U.S. Cl.
  CPC ......... *G01N 21/3518* (2013.01); *G01N 21/47* (2013.01); *G01N 33/004* (2013.01)

(58) Field of Classification Search
  CPC ... G01N 21/3518; G01N 21/47; G01N 33/004
  See application file for complete search history.

(56) References Cited

U.S. PATENT DOCUMENTS 5,009,493 A * 4/1991 Koch .................. G01N 21/031
  356/246
5,326,531 A * 7/1994 Hahn .................. A61B 5/1455
  385/123

(Continued)

OTHER PUBLICATIONS

Kim et al., Enhanced Characteristics of Nondispersive Infrared CO2 Gas Sensor by Deposition of Hydrophobic Thin Film, Aug. 17, 2017, Proceedings, pp. 1-5.*

*Primary Examiner* — Christine S Kim
(74) *Attorney, Agent, or Firm* — Novick, Kim & Lee, PLLC; Jae Youn Kim

(57) ABSTRACT

Provided is a white-cell type non-dispersive infrared gas sensor and more particularly, a non-dispersive infrared carbon dioxide gas sensor deposited with a hydrophobic thin film. To this end, in a carbon dioxide gas sensor for measuring a concentration of carbon dioxide included in gas, the gas sensor is a white-cell type, in the white-cell, first and second reflectors 120 and 130 are disposed to face a third reflector 140, a light source 110 is provided at one side of the third reflector 140 and a first detector 150 and a second detector 160 are provided at the other side. Further, a first hydrophobic thin film 122 may be deposited on the entire reflection surface of the first reflector 120, a second hydrophobic thin film 132 may be deposited on the entire reflection surface of the second reflector 130, and a third hydrophobic thin film 142 may be deposited on the entire reflection surface of the third reflector 140.

11 Claims, 20 Drawing Sheets

(56) References Cited

U.S. PATENT DOCUMENTS

| | | | |
|---|---|---|---|
| 6,410,918 B1 * | 6/2002 | Kouznetsov | G01N 21/3504 250/343 |
| 2016/0151009 A1 * | 6/2016 | Rudmann | G01N 21/3504 600/322 |

* cited by examiner

NON-DISPERSIVE INFRARED CARBON DIOXIDE GAS SENSOR WITH DEPOSITED HYDROPHOBIC THIN FILM

CROSS-REFERENCE TO RELATED APPLICATIONS

This application claims the priority of Korean Patent Application No. 10-2017-0082522 filed on 29 Jun. 2017, in the Korean Intellectual Property Office, the disclosure of which is incorporated herein by reference.

BACKGROUND

Field

The present disclosure relates to a white-cell type non-dispersive infrared gas sensor, and more particularly to a non-dispersive infrared carbon dioxide gas sensor deposited with a hydrophobic thin film.

The present disclosure improves sensitivity and accuracy of a sensor by depositing a hydrophobic substance thin film on a reflector of a non-dispersive infrared gas sensor having an optical structure using a white-cell structure and relates to measurement of gas concentration and correction of disturbance using the same.

Description of the Related Art

In general, a non-dispersive infrared absorption gas sensor (NDIR) measures a concentration of gas by using an optical structure while infrared emitted from a light source reaches an infrared detector (alternatively, sensor). FIG. 1 is a diagram describing a principle of measuring a concentration of a white-cell type in non-dispersive infrared absorption gas sensors in the related art. As illustrated in FIG. 1, a white-cell structure is proposed by White, John U. (Journal of the Optical Society of America, 1942).

The white-cell structure is configured by three concave mirrors having the same radius of curvature, a light source 10, and a detector 50. On the opposite surface of the light source 10, first and second reflectors 20 and 30 are positioned in parallel and a third reflector 40 is positioned to face the first and second reflectors 20 and 30. At this time, the separation of the center of curvature of the first and second reflectors 20 and 30 in the center, a separation length thereof, and an angle between an incident optical axis and a horizontal plane are the most important, thereby determining the reflection number of incident light and adjusting an optical path length.

The light source 10 irradiates infrared light 15 at a predetermined angle at any point of the side of the third reflector 40. Thereafter, the infrared light 15 is reflected by the first reflector 20 (②), repetitively reflected between the third reflector 40 and the first and second reflectors 20 and 30 (③ to ⑧), and then incident to the detector 50. In this case, while the infrared light 15 passes through the gas, an output voltage of the detector 50 varies according to a concentration of carbon dioxide included in the gas.

Such a white-cell structure may be used to observe a very weak spectrum or a spectrum which belongs to a compound that may be obtained only at a low concentration, and may be used for all gases or liquids that come into direct contact with a mirror surface without damaging the mirror surface.

However, such a non-dispersive infrared absorption gas sensor is effective in measuring the concentration of gas, but in the case of a thermopile, when there is a temperature difference between both ends of the metal, 1) an amount of light is measured using a Seebeck effect in which an electromotive force proportional to the temperature difference occurs at both ends, and thus, there is a limitation in that the thermopile can not actively cope with a change in temperature. In addition, 2) there are problems in that the absorption rate of the infrared light is changed, and the output characteristic is changed due to surface contamination of an infrared filter for a gas sensor and contamination and corrosion of the reflector.

In addition, when the temperature is changed while an external state is a state of high temperature and high humidity and toxic gas (acidic or basic toxic gas), the steam is condensed in the reflector, and as a result, a required output is deteriorated by scattering of the infrared light radiated from the light source, and thus, there is a problem in that it is impossible to accurately measure the concentration of gas or an additional correction operation is required.

Accordingly, it is necessary that an optical system of the non-dispersive infrared absorption gas sensor needs to be manufactured to have a structure which may exclude an effect by condensation of moisture while having an anti-chemical structure.

SUMMARY

Therefore, in order to solve the problems above, a first object to be achieved by the present disclosure is to provide a non-dispersive infrared carbon dioxide gas sensor deposited with a hydrophobic thin film capable of preventing corrosion of a reflector and dew formation of steam by depositing the hydrophobic thin film on the surface of the reflector and more accurately measuring a concentration of gas by improving the sensitivity and accuracy of the sensor.

A second object to be achieved by the present disclosure is to provide a non-dispersive infrared carbon dioxide gas sensor deposited with a hydrophobic thin film capable of improving sensitivity of the sensor by reducing a temperature dependency of a reference infrared sensor.

A third object to be achieved by the present disclosure is to provide a non-dispersive infrared carbon dioxide gas sensor deposited with a hydrophobic thin film capable of measuring a concentration of gas by correcting disturbance of the non-dispersive infrared gas sensor.

According to an aspect of the present disclosure, there is provided a non-dispersive infrared carbon dioxide gas sensor deposited with a hydrophobic thin film. In the carbon dioxide gas sensor for measuring a concentration of carbon dioxide included in gas, the gas sensor is a white-cell type, in the white-cell, the first and second reflectors 120 and 130 may be disposed to face a third reflector 140, a light source 110 may be provided at one side of the third reflector 140 and a first detector 150 and a second detector 160 may be provided at the other side, and at least a part of the reflection surfaces of the first, second, and third reflectors 120, 130, and 140 may be deposited with a hydrophobic thin film.

Further, a first hydrophobic thin film 122 may be deposited on the entire reflection surface of the first reflector 120, a second hydrophobic thin film 132 may be deposited on the entire reflection surface of the second reflector 130, and a third hydrophobic thin film 142 may be deposited on the entire reflection surface of the third reflector 140.

Further, the hydrophobic thin film may include one of parylene, OTS, fluorine silane, and the like and more preferably parylene-C.

The deposition thickness of the parylene-C may be 0.2 μm to 0.7 μm and more preferably 0.5 μm.

Further, the second detector 160 may be a reference detector, and a Fresnel lens 152 may be further provided in front of the first detector 150.

Further, the second detector 160 may be a reference detector, and a protective window 115 and a hollow disk 167 may be further provided in front of the second detector 160.

In addition, a protective window 115 may be further provided in front of the light source 110.

In addition, a heater may be further mounted in the vicinity of the first, second, and third reflectors 120, 130, and 140.

Further, a second heater 240 may be further mounted in the vicinity of the first and second reflectors 120 and 130, and a first heater 230 may be further mounted in the vicinity of the third detector 140.

According to an exemplary embodiment of the present disclosure, it is possible to improve sensitivity and accuracy of the sensor by depositing or coating a hydrophobic thin film on the surface of a reflector having a white-cell structure.

Further, it is possible to adjust an output of a reference infrared sensor which is insensitive to a change in temperature by controlling an energy density which reaches each gas sensor from a light source to a reflector, perform an output voltage generated by the incident energy, transformation, calculation, and conversion, and determine and correct sensor output compensation or aged deterioration according to an ambient temperature.

BRIEF DESCRIPTION OF THE DRAWINGS

The above and other aspects, features and other advantages of the present disclosure will be more clearly understood from the following detailed description taken in conjunction with the accompanying drawings, in which:

FIGS. 9A and 9B illustrate an incident amount of energy when a continuous wavelength emitted from the light source 110 reaches the first and second detectors 150 and 160 through simulation analysis, in which FIG. 9A illustrates an incident amount of energy which reaches the first detector 150, and FIG. 9B illustrates a simulation analysis result illustrating an incident amount of energy which reaches the second detector (reference detector) 160;

FIGS. 12A and 12B are graphs illustrating differential amplification of output voltages of the first detector 150 and the second detector 160, in which FIG. 12A illustrates a gas sensor using a reflector deposited with a hydrophobic thin film according to an exemplary embodiment of the present disclosure and FIG. 12B illustrates a gas sensor using a general reflector;

DETAILED DESCRIPTION OF THE PREFERRED EMBODIMENT

Figure 1:
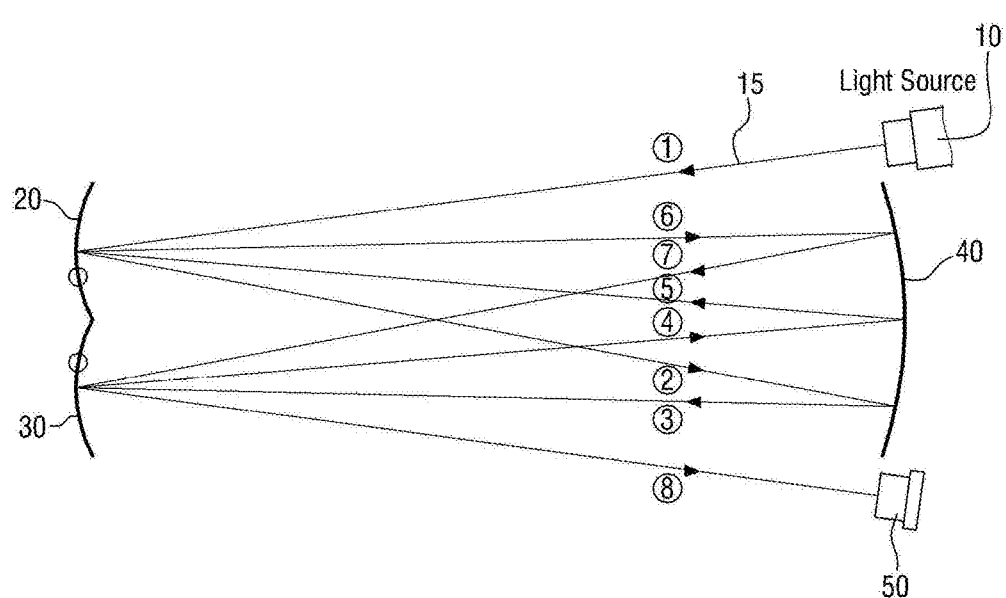
FIG. 1 is a diagram describing a principle of measuring a concentration of a white-cell type in non-dispersive infrared absorption gas sensors in the related art.

Hereinafter, configurations of the present disclosure will be described in more detail with reference to the accompanying drawings. The present disclosure may have various modifications and various exemplary embodiments and specific exemplary embodiments will be illustrated in the drawings and described in detail.

In the present application, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Unless otherwise defined, all terms used herein including technological or scientific terms have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined here.

Configuration of Gas Sensor

Figure 2:
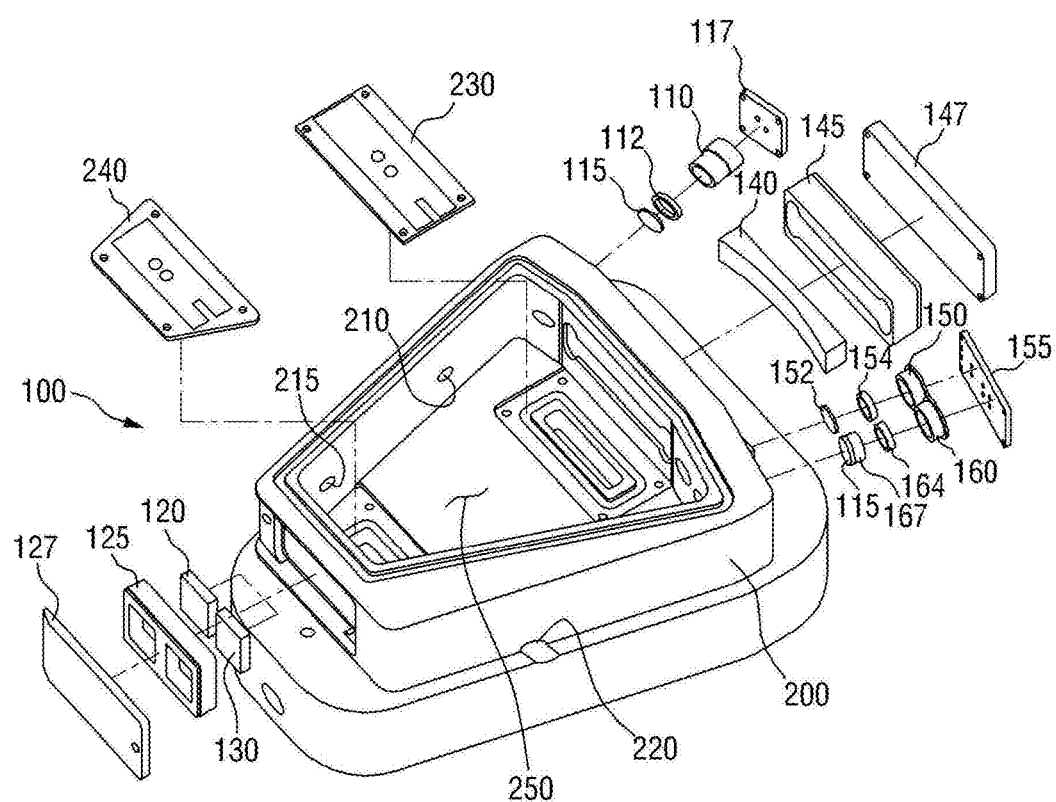
FIG. 2 is an exploded perspective view of a non-dispersive infrared carbon dioxide gas sensor deposited with a hydrophobic thin film according to an exemplary embodiment of the present disclosure.
Figure 3:
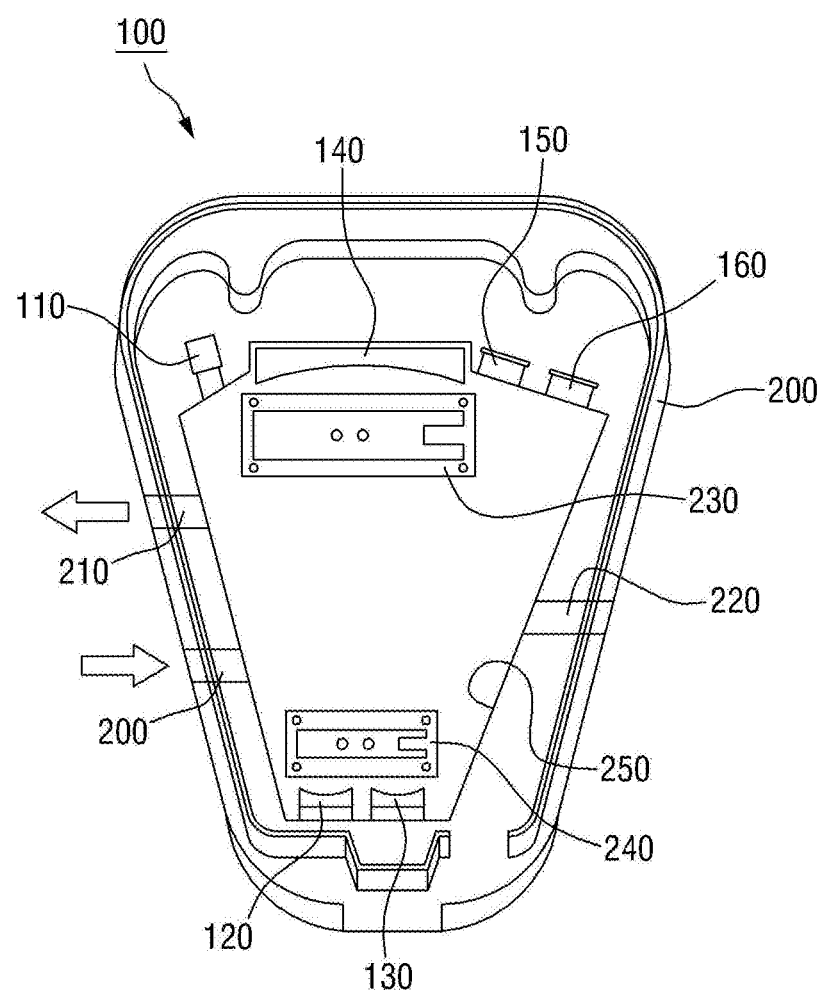
FIG. 3 is a plan view of the gas sensor illustrated in FIG. 2.

FIG. 2 is an exploded perspective view of a non-dispersive infrared carbon dioxide gas sensor deposited with a hydrophobic thin film according to an exemplary embodiment of the present disclosure and FIG. 3 is a plan view of the gas sensor illustrated in FIG. 2.

As illustrated in FIGS. 2 and 3, a housing 200 is made of metal or a synthetic resin material and has a structure which maintains airtightness of a chamber 250 formed therein.

The light source 110 is an infrared light source that emits continuous infrared light having a wavelength of 0 to 10 μm and is positioned at one side of the third reflector 140 and positioned to be irradiated to the first and second reflectors 120 and 130. A first PCB 117 is a circuit board for fixing and driving the light source 110. An O-ring 112 maintains the airtightness of the chamber 250 and prevents gas from being leaked. A protective window 115 is mounted to prevent a change in temperature of the light source 110 due to the temperature of the gas when the gas is introduced, and a sapphire window is an example.

The first reflector 120 has the same radius of curvature as that of the second and third reflectors 130 and 140 and has about half of the size of the third reflector 140. The first and second reflectors 120 and 130 have the same size and are arranged in parallel toward the light source 110. A reflector fixture 125 fixes the positions of the first and second reflectors 120 and 130 and a first cover 127 fixes the position of the reflector fixture 125.

The third reflector 140 is positioned on the opposing surfaces of the first and second reflectors 120 and 130 and is relatively longer (about two times) than the first and second reflectors 120 and 130. A third reflector fixture 145 fixes the position of the third reflector 140 and a second cover 147 fixes the position of the third reflector fixture 145.

The first, second, and third reflectors 120, 130, and 140 are general reflectors based on SiOx/Au/Cr on fused silica.

The first detector 150 is provided on the other side of the third reflector 140 as an infrared sensor for measuring the concentration of carbon dioxide. The first detector 150 may be implemented as a thermopile or pyroelectric sensor. The O-ring 154 maintains airtightness to prevent the gas from being leaked. A Fresnel lens 152 is positioned in front of the first detector 150 and used for focusing the incident energy incident to the first detector 150.

The second detector 160 is provided in parallel with the first detector 150 as a reference sensor for detecting infrared light having a central wavelength of 3.91 μm. The second detector 160 may be implemented as a thermopile or pyroelectric sensor. The O-ring 164 maintains airtightness to prevent the gas from being leaked. The protective window 115 is mounted for preventing damage to an optical filter of the thermopile or pyroelectric sensor due to gas when toxic and corrosive gas is introduced and a sapphire window is an example. The hollow disk 167 is in the form of a disk having a through hole formed at the center thereof to reduce the amount of incident energy reaching the second detector (reference sensor) 160. The second PCB 155 is a circuit board for fixing and driving the first and second detectors 150 and 160.

A gas inlet 215 is through-formed on one side of the housing 200 to allow inflow of the gas and a gas outlet 210 is through-formed on the other side of the housing 200 to allow outflow of the gas.

A first heater 230 is installed on the bottom surface in contact with the third reflector 140 and prevents moisture from adhering to the third reflector 140 through heating. A second heater 240 is installed on the bottom surface in contact with the first and second reflectors 120 and 130 and prevents moisture from adhering to the first and second reflectors 120 and 130 through heating.

A temperature sensor 220 extends to the chamber 250 through the housing 200 and measures the temperature of the gas or the temperature of the chamber 250.

Figure 4:
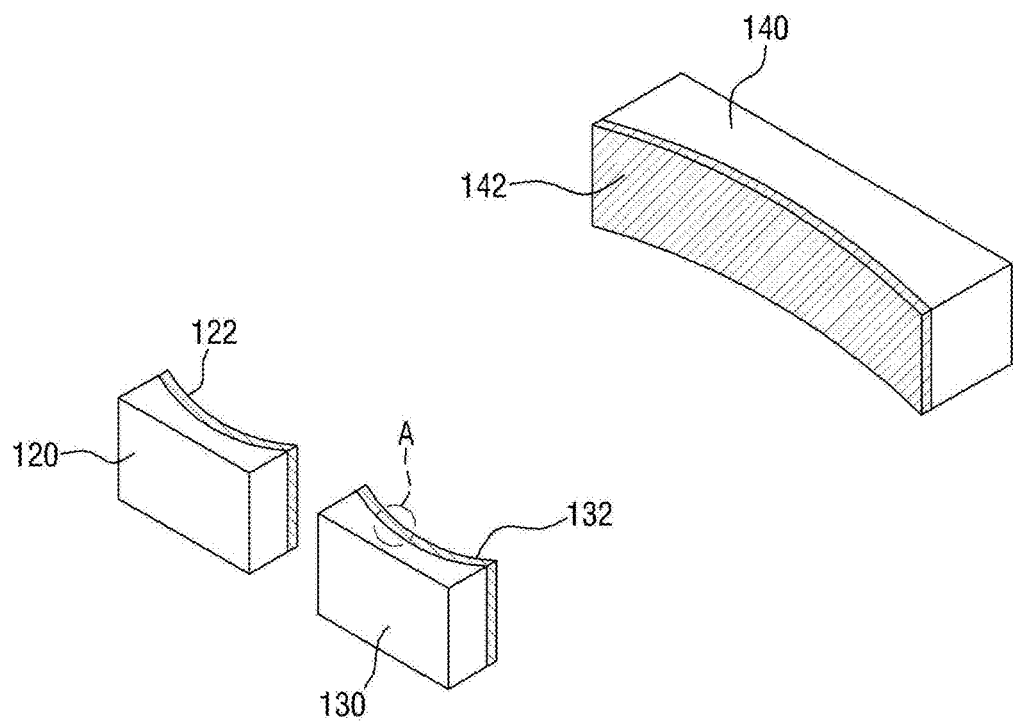
FIG. 4 is a perspective view selectively illustrating only reflectors in the carbon dioxide gas sensor according to the present disclosure.
Figure 5:
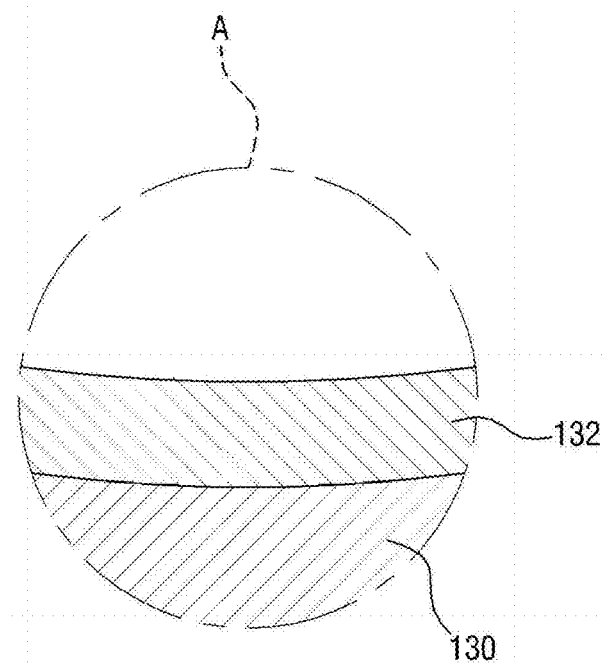
FIG. 5 is a partially enlarged cross-sectional view of an A-portion in FIG. 4.

FIG. 4 is a perspective view selectively illustrating only reflectors in the carbon dioxide gas sensor according to the present disclosure and FIG. 5 is a partially enlarged cross-sectional view of an A-portion in FIG. 4. As illustrated in FIGS. 4 and 5, a first hydrophobic thin film 122 is formed on the surface of the first reflector 120, a second hydrophobic thin film 132 is formed on the surface of the second reflector 130, and a third hydrophobic thin film 142 is formed on the surface of the third reflector 140.

These thin films are hydrophobic, transparent, and chemically resistant and formed through a semiconductor deposition process. Examples of these hydrophobic thin films 122, 132, and 142 include parylene, octadecyltrichlorosilane (OTS), fluorine silane, and the like.

Among them, particularly, parylene-C can be deposited through a semiconductor deposition process with a thickness of 0.2 μm to 0.7 μm. When the thickness is smaller than 0.2 μm, the uniform deposition may be difficult or the hydrophobicity may be deteriorated, and when the thickness exceeds 0.7 μm, the material, the time and the process are wasted due to the unnecessarily thick deposition. The most preferable thickness is 0.5 μm.

Figure 8:
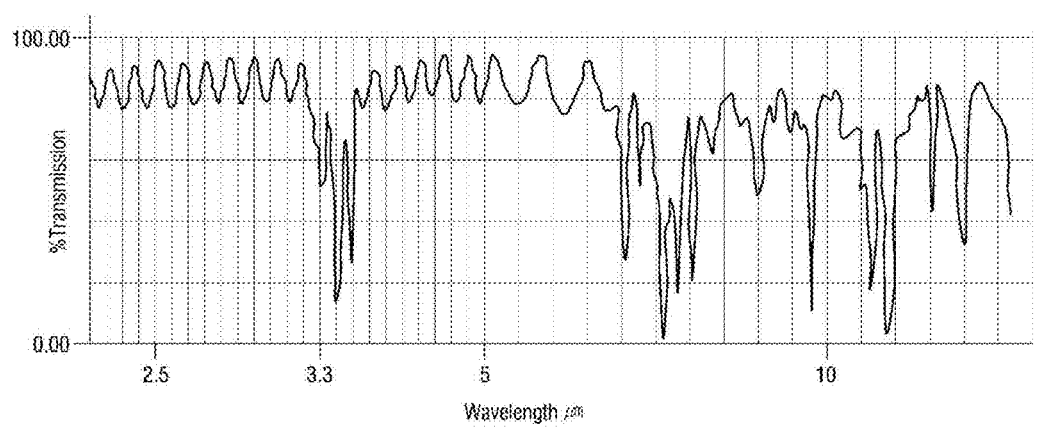
FIG. 8 is a graph illustrating an infrared transmission spectrum of parylene-C in a middle infrared region.

Such a hydrophobic thin film or film is formed by deposition to prevent damage to the surface and vapor condensation due to corrosion of the reflector or chemical reaction of by-products. Particularly, parylene-C may be uniformly deposited as a very thin layer with a thickness of 1 μm or less, has little absorption in the visible region, and is transparent and colorless. It is known that the parylene-C may maintain a current state even though being continuously exposed to air for 10 years at 100° C. and is insoluble in all organic solvents within 150° C. Further, the parylene-C is a material that has a characteristic of no condensation of moisture by high temperature and high humidity and has a transparency of 80% or more in the middle infrared region. For reference, FIG. 8 is a graph illustrating an infrared transmission spectrum of parylene-C in a middle infrared region.

Figure 6:
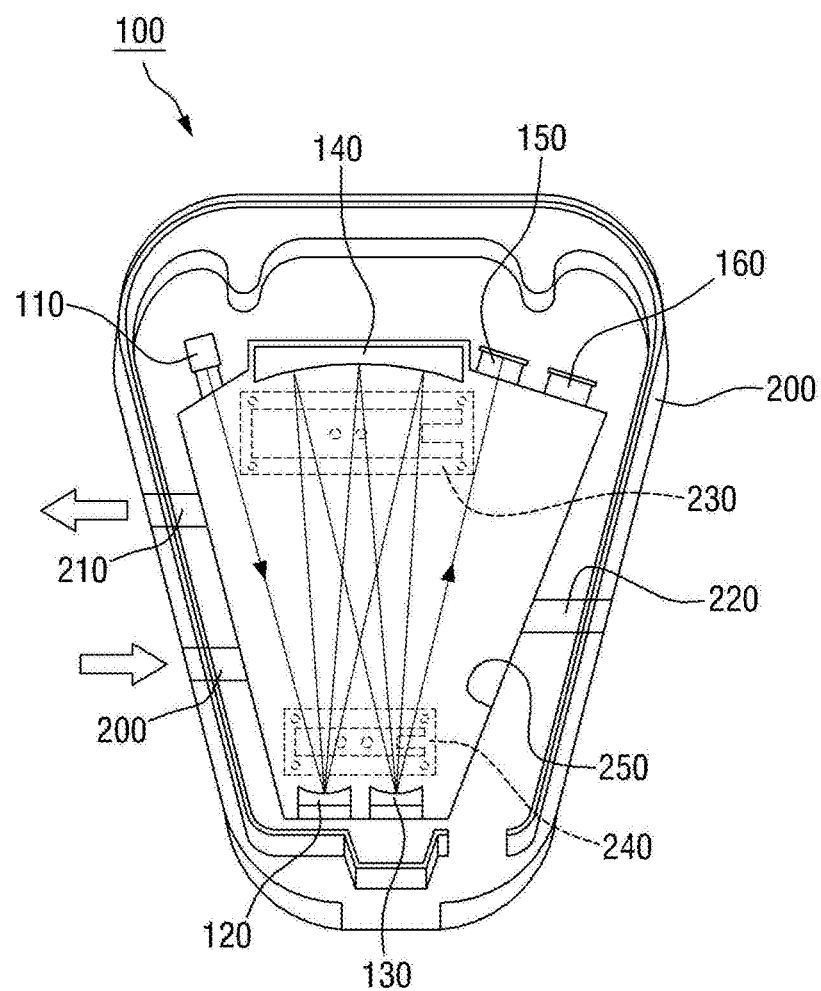
FIG. 6 is a plan view illustrating a path of infrared light which is incident to a first detector 150 in the gas sensor according to the exemplary embodiment of the present disclosure.
Figure 7:
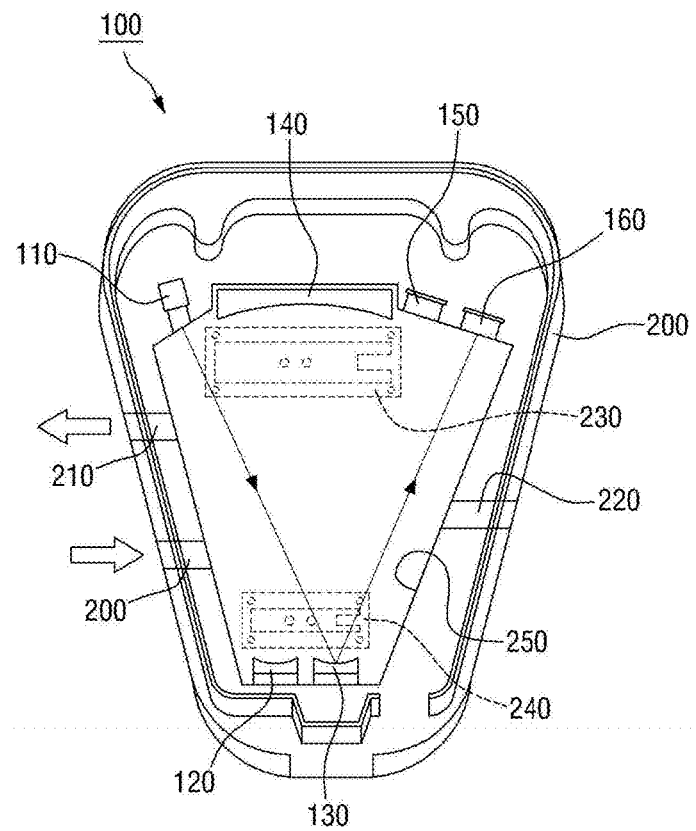
FIG. 7 is a plan view illustrating a path of infrared light which is incident to a second detector (a reference detector) 160 in the gas sensor according to the exemplary embodiment of the present disclosure.

FIG. 6 is a plan view illustrating a path of infrared light which is incident to a first detector 150 in the gas sensor according to the exemplary embodiment of the present disclosure and FIG. 7 is a plan view illustrating a path of infrared light which is incident to a second detector (a reference detector) 160 in the gas sensor according to the exemplary embodiment of the present disclosure. As illustrated in FIGS. 6 and 7, the infrared light irradiated from the light source 110 is reflected to the first detector 150 through several times of reflections, and some of the infrared light irradiated from the light source 110 is reflected to the second reflector (reference detector) 160 after being reflected only once through the second detector 130. The first and second detectors 150 and 160 are disposed at two points thereof to detect the concentration of the gas (e.g., carbon dioxide) by analyzing the output voltage according to the amount of energy that is incident to the first and second detectors 150 and 160 from the light source 110 and the gas concentration.

Measurement of Gas Concentration

The output characteristics of the non-dispersive infrared gas sensor 100 are given by the energy emitted from the light source 110, the infrared absorption and emission in a medium, and the amount of energy incident to the first and second detectors 150 and 160. The Beer-Lambert law widely applied in the infrared gas sensor 100 is represented by Equation 1.

$$I = I_0 \exp(-\alpha x l) \quad \text{[Equation 1]}$$

Herein, $I_0$ represents an initial light intensity, $\alpha$ represents a light absorption coefficient of a specific gas, x represents a gas concentration, and I represents an optical path. When the same absorption coefficient and the same concentration are applied from the infrared light source 110 to the detectors 150 and 160, an energy reduction width may be increased with respect to a change in gas concentration by lengthening the optical path. Since the energy of the incident light is large to be insensitive to external noise, it is easy to be applied as an optical gas sensor. In addition, when the reflector with the hydrophobic thin film is used, it is possible to secure a state in which the amount absorbed during reflection may be minimized, and to ensure chemical resistance by preventing contamination and corrosion in the atmosphere. In addition, it is possible to minimize scattering of infrared light due to adhesion of steam and errors caused by energy loss according to the scattering.

Figure 9A:
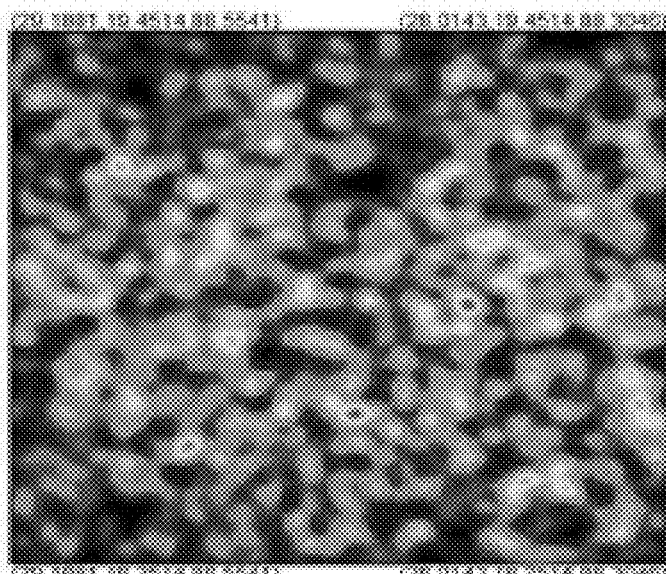
Figure 9B:
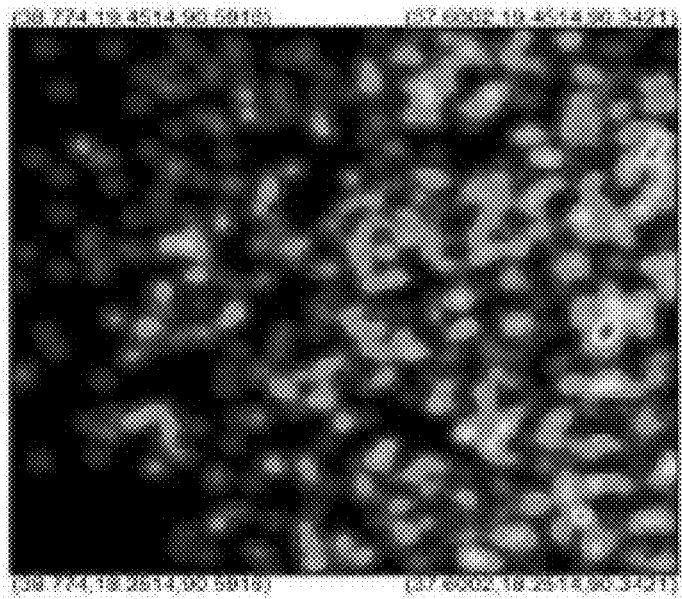

FIGS. 9A and 9B illustrate an incident amount of energy when a continuous wavelength emitted from the light source 110 reaches an infrared filter transmission region of the first and second detectors 150 and 160 as infrared sensors through simulation analysis. FIG. 9A illustrates an incident amount of energy which reaches the first detector 150, and FIG. 9B illustrates an incident amount of energy which reaches the second detector (reference detector) 160.

In the simulation analysis, as illustrated in FIGS. 6 and 7, the light emitted from the light source 110 is focused in active regions of the first and second detectors 150 and 160. In an exemplary embodiment of the present disclosure, since the output voltage emitted from the first and second detectors 150 and 160 is differentially amplified or the ratio of the output voltage is calculated and used, in order to increase a change width, the second detector 160 is located at a portion where the incident amount of energy is less than that of the first detector 150 for detecting $CO_2$ gas.

The voltage output from the infrared sensor by the infrared energy density is drawn from the following Equation 2 proposed by SeungHwan Yi (Korea Sensor Society, 2016 and Sensors and Materials, 2017).

$$V_{out}(T,x) = V_{band}(T) + V_{gas}(T) \exp(-k(T)x) \quad \text{[Equation 2]}$$

Herein, $V_{out}$ represents an output voltage of the detector, $V_{band}$ represents a voltage indicating an infrared energy density other than an absorption wavelength of target gas (e.g., carbon dioxide), $V_{gas}$ represents a voltage indicating an infrared energy density absorbed by the target gas, and k represents the product of the optical path and the absorption coefficient.

Figure 10:
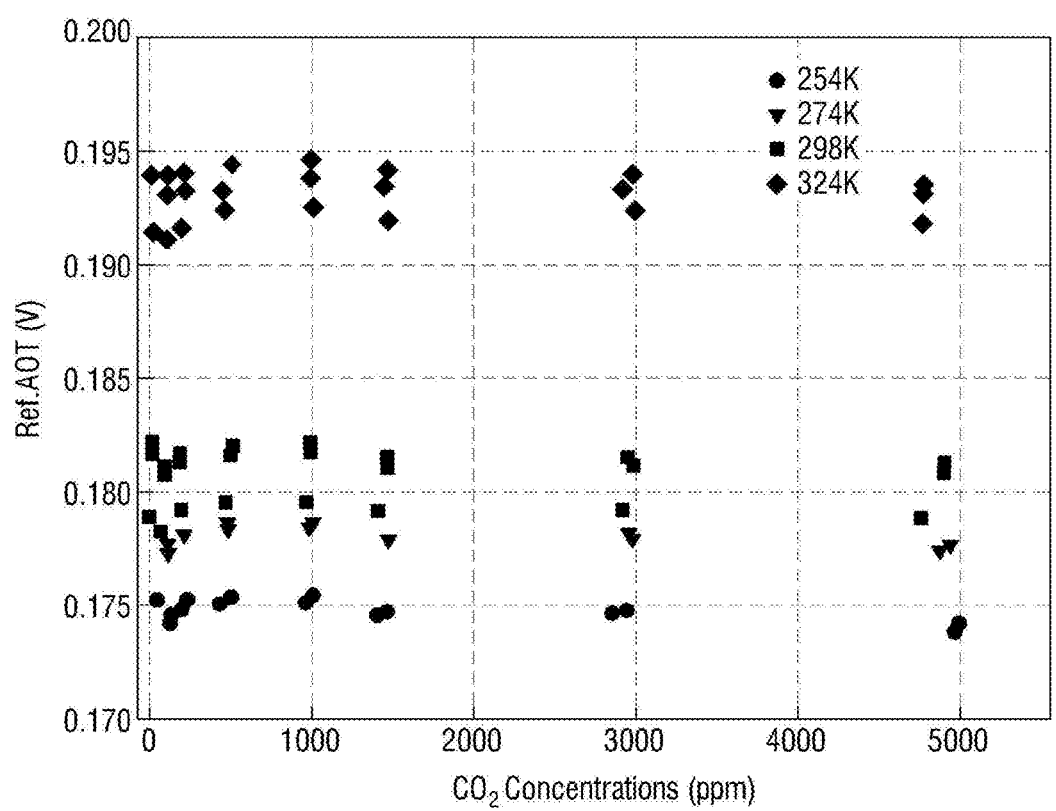
FIG. 10 is a graph illustrating an increase characteristic of an output voltage according to an increase in temperature with respect to the second detector (reference sensor) which is a configuration of the present disclosure.

However, the second detector (reference sensor), which is irrelevant to gas components in the atmosphere, has an output characteristic irrelevant to the change in gas concentration, but as illustrated in FIG. 10, it is known that there is a characteristic that the output voltage increases with temperature when the temperature increases. FIG. 10 is a graph illustrating an increase characteristic of an output voltage according to an increase in temperature with respect to the second detector (reference sensor) 160 which is a configuration of the present disclosure.

Figure 11A:
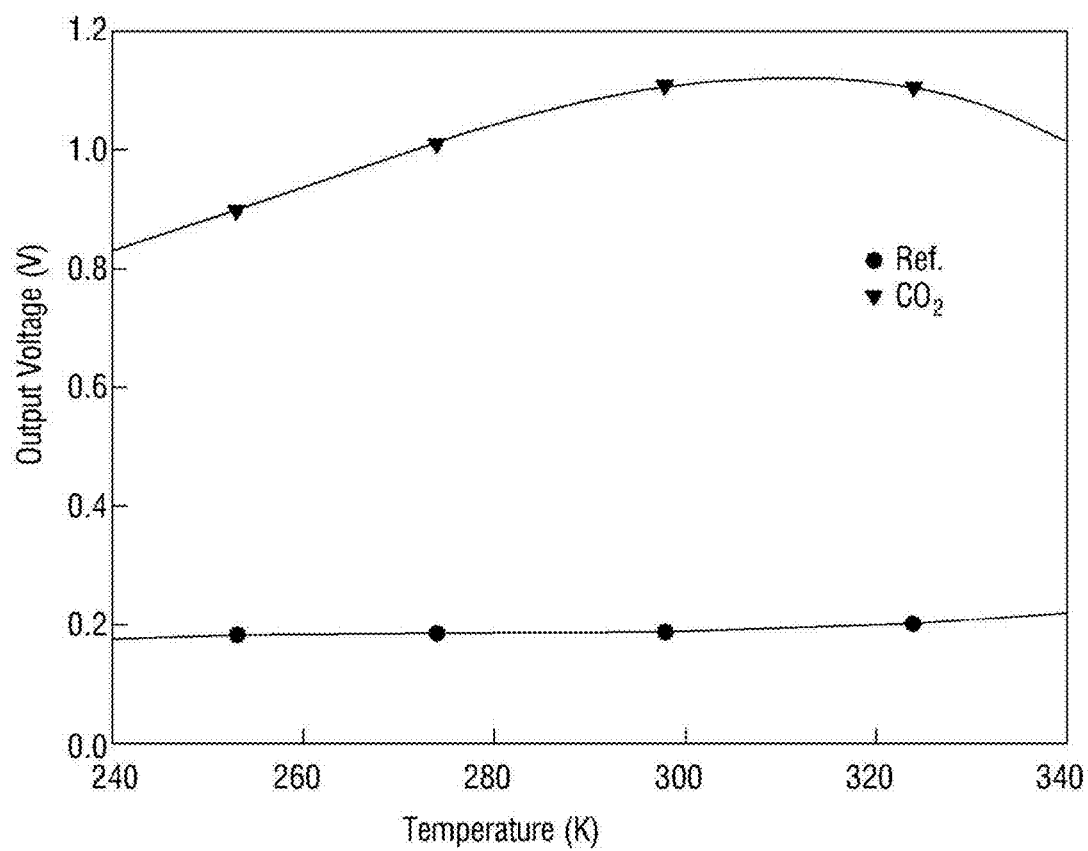
FIG. 11A is a graph illustrating output voltages of the first detector 150 and the second detector (reference sensor) 160 when target gas is 0 ppm.
Figure 11B:
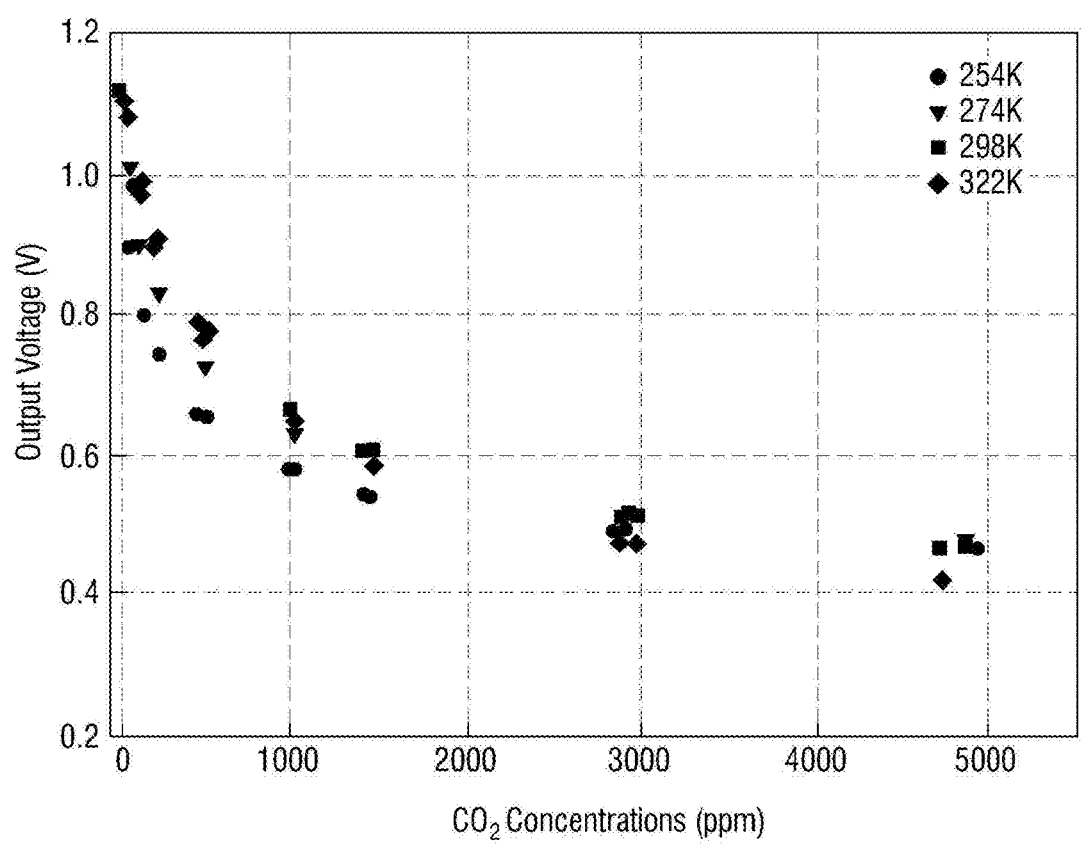
FIG. 11B is a graph illustrating an output voltage of the first detector 150 according to changes in temperature and gas concentration.
Figure 11C:
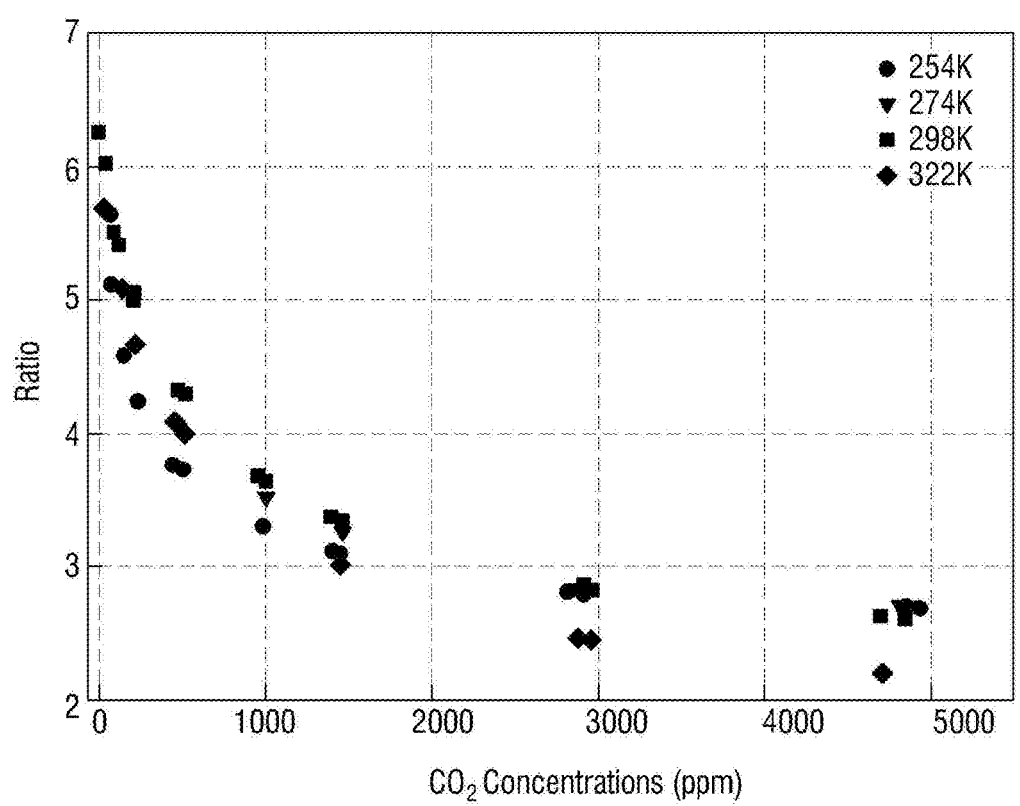
FIG. 11C is a graph illustrating a ratio $R=(V_{co2})/(V_{Ref})$ of output voltages between the second detector 160 and the first detector 150, when a hollow disk 163 for reducing an incident energy amount reaching the second detector 160 is not used.

As such, the output voltages of the first and second detectors 150 and 160 are represented by a function of the temperature and the gas concentration and an experimental result is illustrated in FIG. 11. More particularly, FIG. 11A is a graph illustrating output voltages of the first detector 150 and the second detector (reference sensor) 160 when target gas is 0 ppm, FIG. 11B is a graph illustrating an example of an output voltage of the first detector 150 according to changes in temperature and gas concentration, and FIG. 11C is a graph illustrating a ratio $R = (V_{co2})/(V_{Ref})$ of output voltages between the second detector 160 and the first detector 150, when a hollow disk 163 for reducing an incident energy amount reaching the second detector 160 is not used.

Figure 12A:
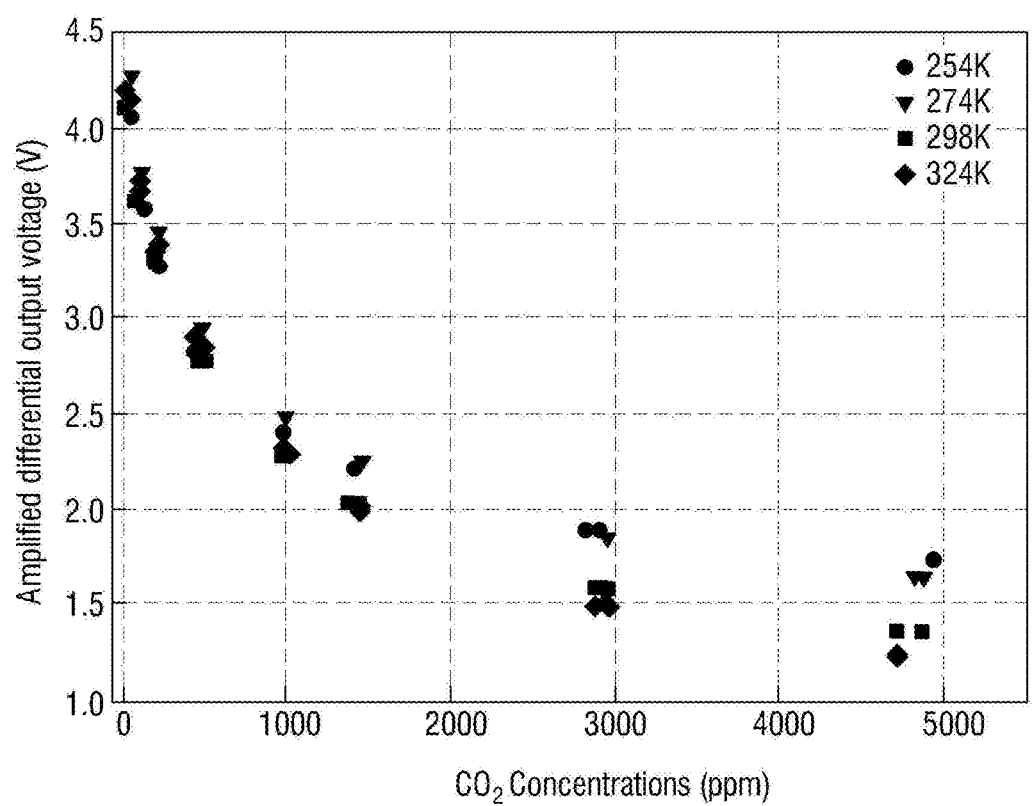
Figure 12B:
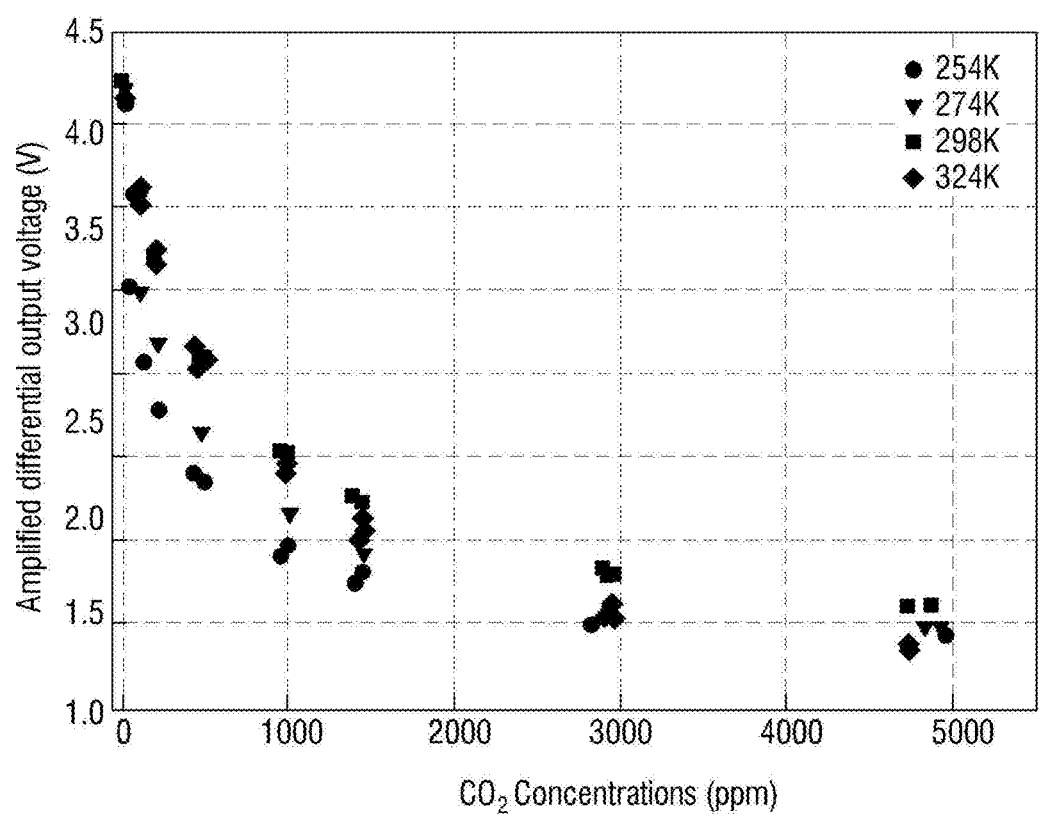

FIGS. 12A and 12B are graphs illustrating differential amplification of output voltages of the first detector 150 and the second detector 160, in which FIG. 12A illustrates a gas sensor using a reflector deposited with a hydrophobic thin film according to an exemplary embodiment of the present disclosure and FIG. 12B illustrates a gas sensor using a general reflector. As illustrated in FIGS. 12A and 12B, it can be seen that the output voltage exponentially decreases as the gas concentration increases, and it can be seen that the gas sensor 100 in which the hydrophobic thin film is deposited on the reflector according to the present disclosure has an apparent temperature dependent characteristic compared to the general gas sensor.

Figure 13A:
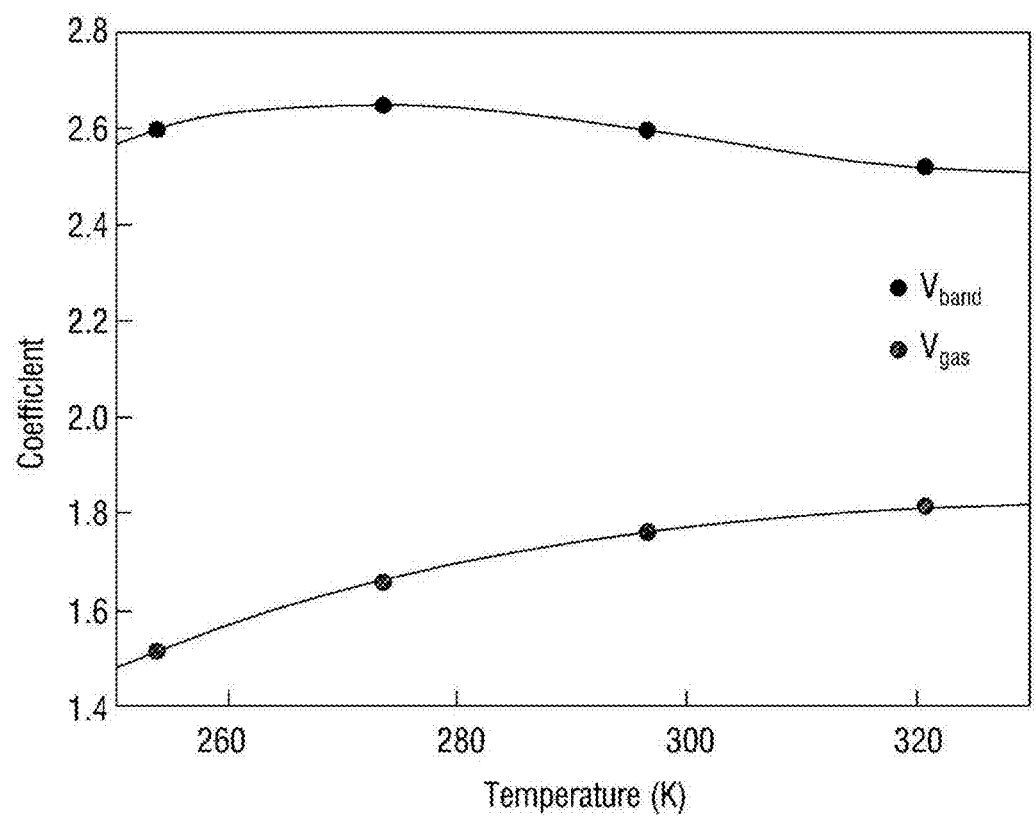
FIG. 13A is a graph illustrating characteristics of output voltages $V_{band}$ and $V_{gas}$ according to a change in temperature.
Figure 13B:
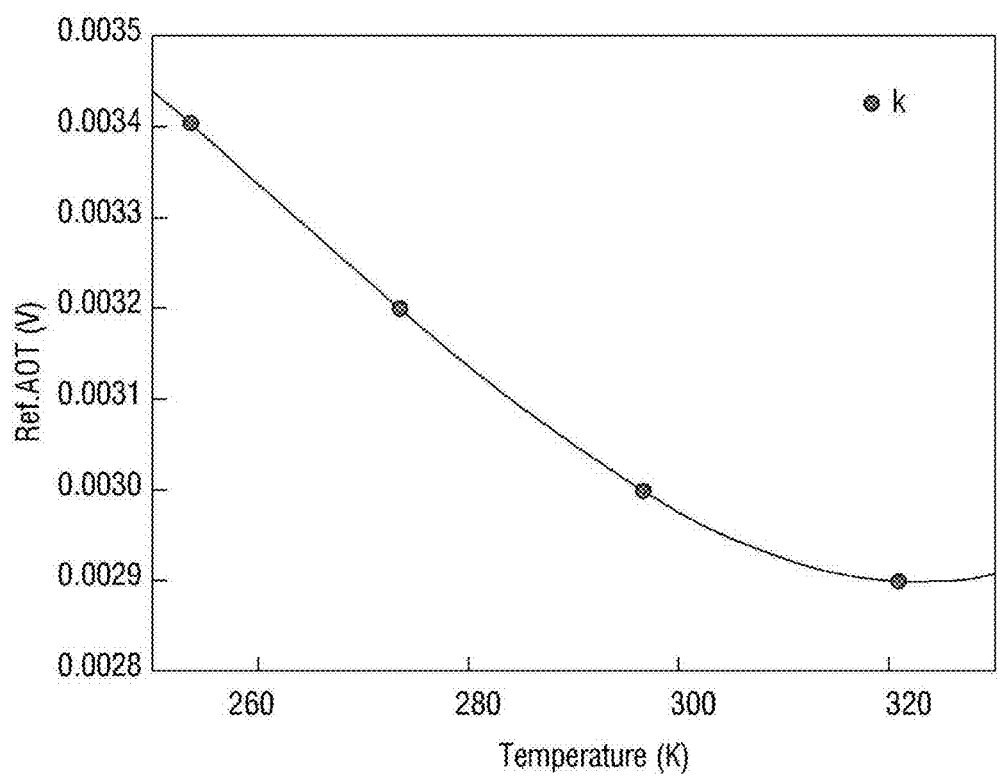
FIG. 13B is a graph illustrating that k (the product of an optical path and an absorption coefficient) is represented by quadratic and cubic functions according to a change in temperature.

As illustrated in FIG. 12A, in the case of the gas sensor 100 in which the hydrophobic thin film of the present disclosure (e.g., parylene-C) is deposited, as the temperature increases, the change width of the output voltage increases. However, as illustrated in FIG. 12B, in the case of the gas sensor using the general reflector, it can be seen that as the gas concentration increases, the change width of the voltage is larger than that of FIG. 12A, but the output characteristic according to a change in temperature is not apparently shown. At this time, the output voltages $V_{band}$ and $V_{gas}$ and the product k of the optical path and the absorption coefficient are represented in the form of quadratic and cubic functions, as illustrated in FIGS. 13A and 13B. FIG. 13A is a graph illustrating characteristics of the output voltages $V_{band}$ and $V_{gas}$ according to a change in temperature and FIG. 13B is a graph illustrating that k (the product of the optical path and the absorption coefficient) is represented by quadratic and cubic functions according to a change in temperature.

Experiment of Gas Sensor

Figure 14A:
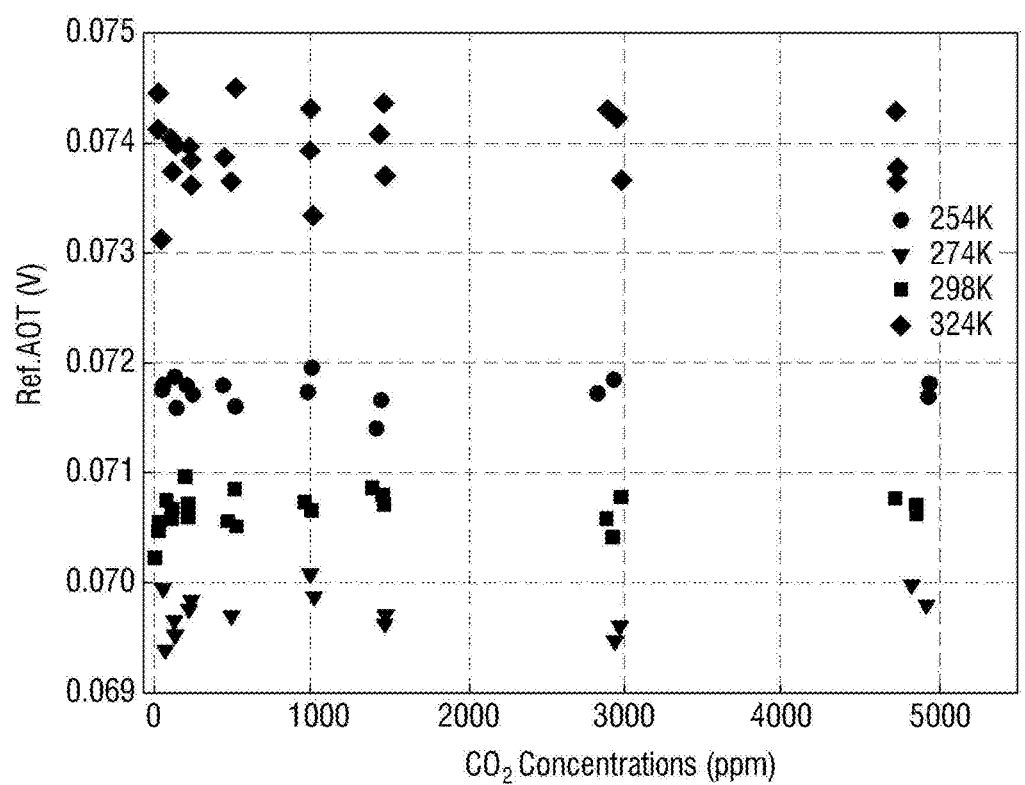
FIG. 14A is a graph illustrating a voltage $V_{Ref}$ output by the second detector (reference sensor) 160 in the gas sensor 100 deposited with the hydrophobic thin film (e.g., parylene-C)
Figure 14B:
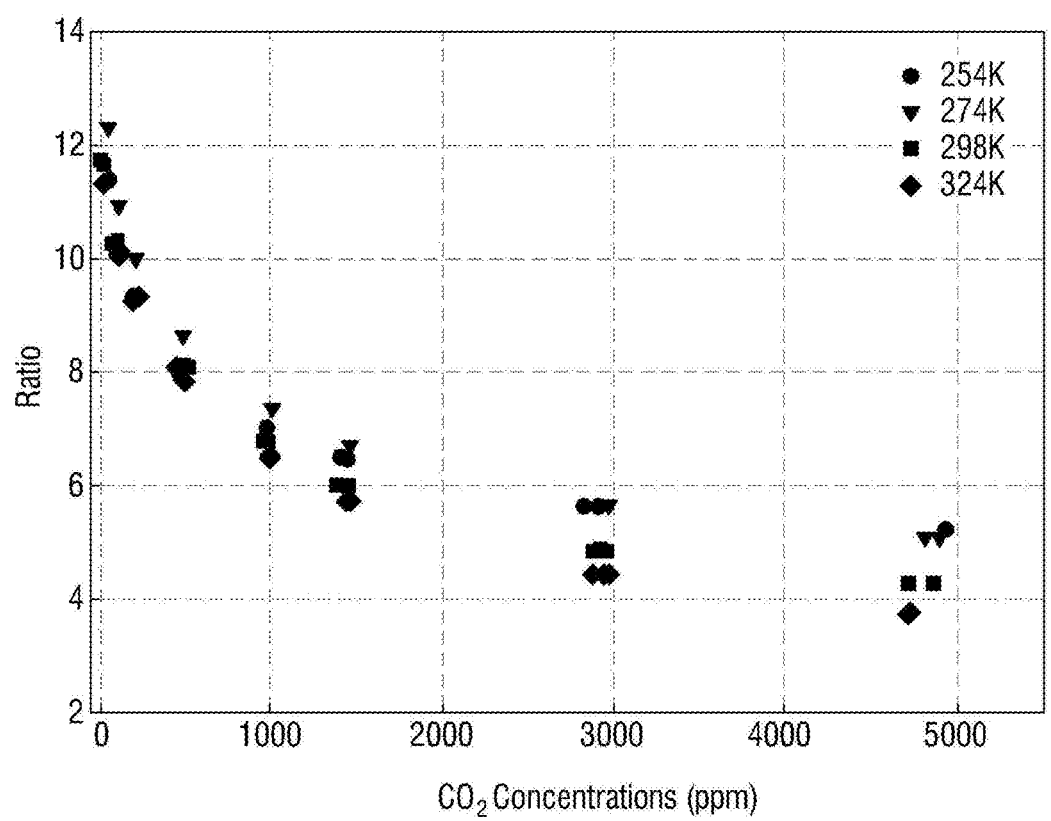
FIG. 14B is a graph illustrating a ratio $R=(V_{co2})/(V_{Ref})$ of the output voltage of the first detector 150 in the gas sensor 100.

FIG. 14A is a graph illustrating a voltage $V_{Ref}$ output by the second detector (reference sensor) 160 in the gas sensor 100 deposited with the hydrophobic thin film (e.g., parylene-C) and FIG. 14B is a graph illustrating a ratio $R = (V_{co2})/(V_{Ref})$ of the output voltage of the first detector 150 in the gas sensor 100.

As illustrated in FIG. 14A, the output voltage of the second detector (reference sensor) 160 varies according to the temperature as illustrated in FIG. 10, and in the present disclosure, the hollow disk 167 is disposed at the front end of the second detector (reference sensor) 160. As a result, even though the temperature is changed by decreasing the amount of energy reaching the second detector (reference sensor) 160 from the light source 110, the change width of the output voltage $V_{Ref}$ of the second detector (reference sensor) 160 is within about 5 mV. For reference, in the case of the conventional structure, as illustrated in FIG. 10, as the temperature increases in an experimental temperature period, the change width of the output voltage increases by a difference of about 20 mV. That is, according to an exemplary embodiment of the present disclosure, it can be seen that the change width of the output voltage $V_{Ref}$ of the second detector (reference sensor) 160 is substantially constant within 1 mV on average even though the temperature and the gas concentration increase.

Further, in FIG. 14B, it is illustrated that the ratio $R=(V_{co2})/(V_{Ref})$ of the voltage output from the first detector 150 is calculated by using this. As illustrated in FIG. 14B, when the ratio is calculated by lowering the output voltage $V_{Ref}$ of the second detector (reference sensor) 160 that is irrelevant to the changes in temperature and gas concentration, the change width according to the gas concentration increases, and as a result, it is possible to improve the accuracy in calculating the gas concentration by improving the quantization level of an A/D converter.

Figure 15:
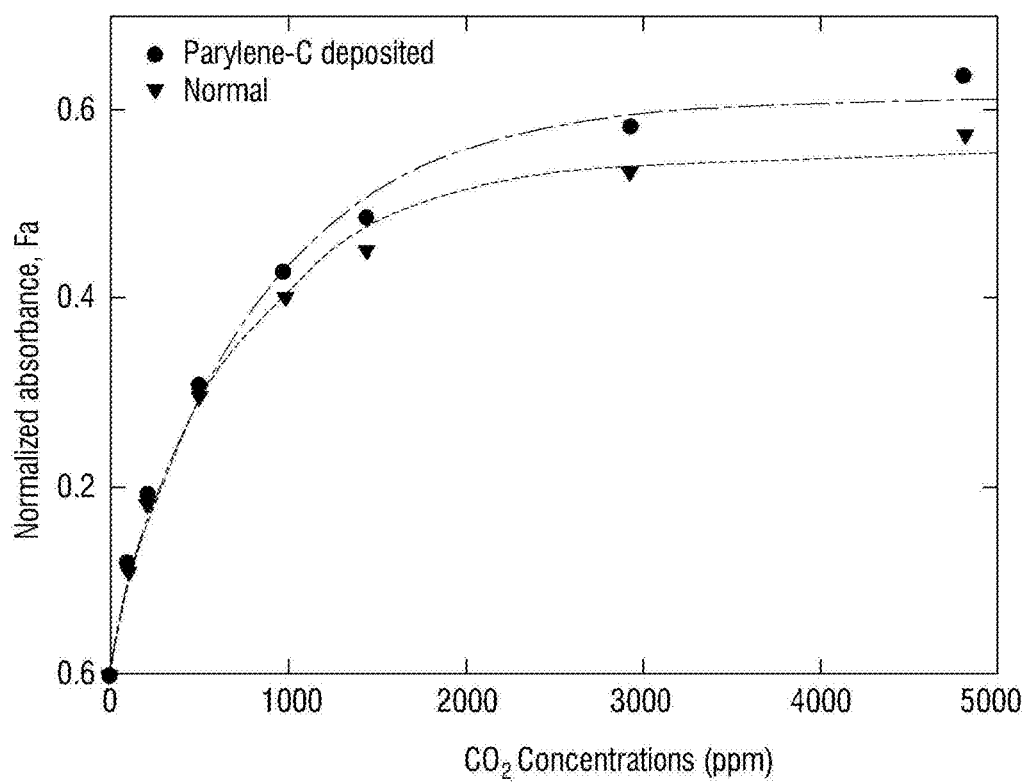
FIG. 15 is a graph illustrating infrared absorbances of a hydrophobic thin film (e.g., parylene-C) deposited on the surface of a reflector and a general reflector (SiOx/Au/Cr on fused-silica) as a function of $CO_2$ concentration at 298 K.

Meanwhile, FIG. 15 illustrates infrared absorbances of a hydrophobic thin film (e.g., parylene-C) deposited on the surface of a reflector having a white-cell structure and a general reflector (SiOx/Au/Cr on fused-silica) as a function of $CO_2$ concentration at 298 K based on the above experimental result and Table 1 illustrates absorbance according to a concentration of $CO_2$ standard gas.

TABLE 1

| | Absorbance | |
| --- | --- | --- |
| ppm | parylene-C | Normal |
| 0 | 0.0000 | 0.0000 |
| 109 | 0.1182 | 0.1075 |
| 222 | 0.1910 | 0.1803 |
| 519 | 0.3097 | 0.2955 |
| 1054 | 0.4238 | 0.4009 |
| 1510 | 0.4845 | 0.4521 |
| 3036 | 0.5837 | 0.5358 |
| 4900 | 0.6356 | 0.5734 |

As illustrated in FIG. 15 and Table 1, it can be seen that in the case of the gas sensor deposited with the hydrophobic thin film, as the concentration increases, the change width and the sensitivity of the absorbance according to a change in $CO_2$ concentration increase compared to the general reflector. Therefore, it can be seen that the non-dispersive infrared carbon dioxide gas sensor deposited with the hydrophobic thin film according to an exemplary embodiment of the present disclosure can easily perform compensation and correction.

Figure 16A:
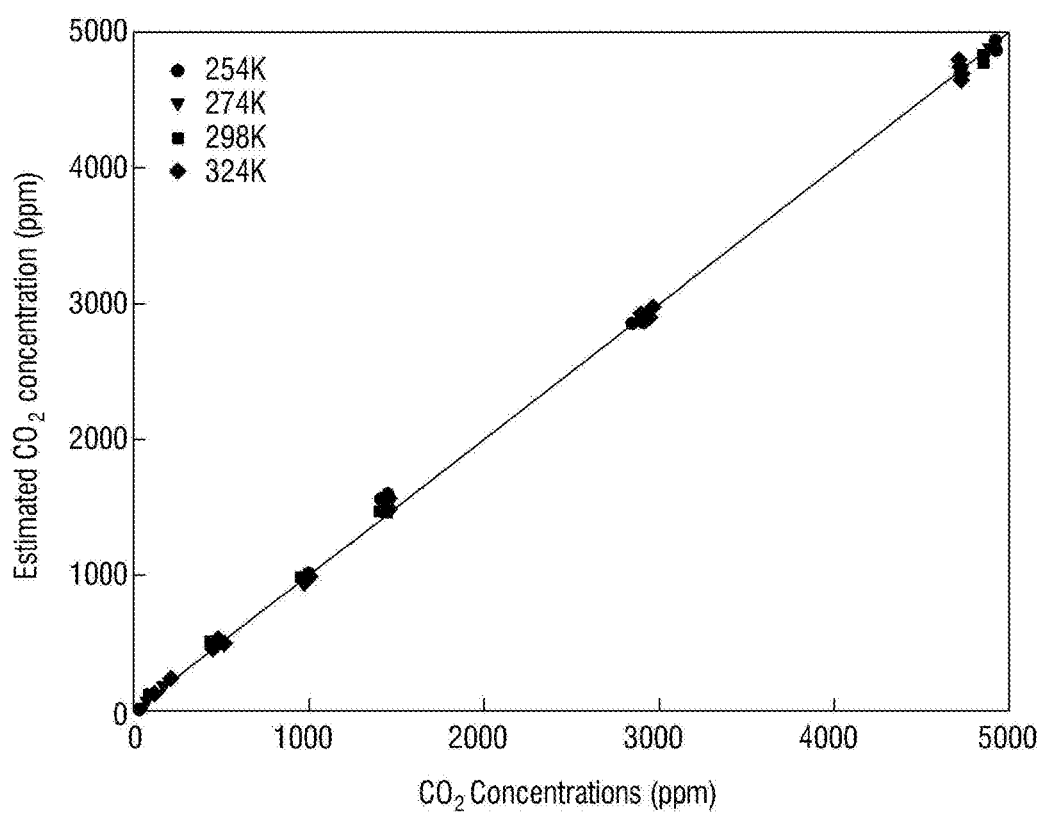
FIG. 16A is a graph illustrating that an estimated concentration calculating by compensating for a temperature by parameters obtained by drawing a trend line from experimental results illustrated in FIGS. 10 to 12 is expressed by Equation 3 and the estimated concentration is drawn through Equation 3.

FIG. 16A illustrates that an estimated concentration calculating by compensating for a temperature by parameters obtained by drawing a trend line from experimental results illustrated in FIGS. 10 to 12 is expressed by Equation 3 and as a result, the estimated concentration is drawn.

$$x(\text{ppm}) = \frac{1}{-k(T)} \left\{ \ln\left[\frac{V_{out}(T, x) - V_{band}(T)}{V_{gas}(T)}\right] \right\} \quad \text{[Equation 3]}$$

Figure 16B:
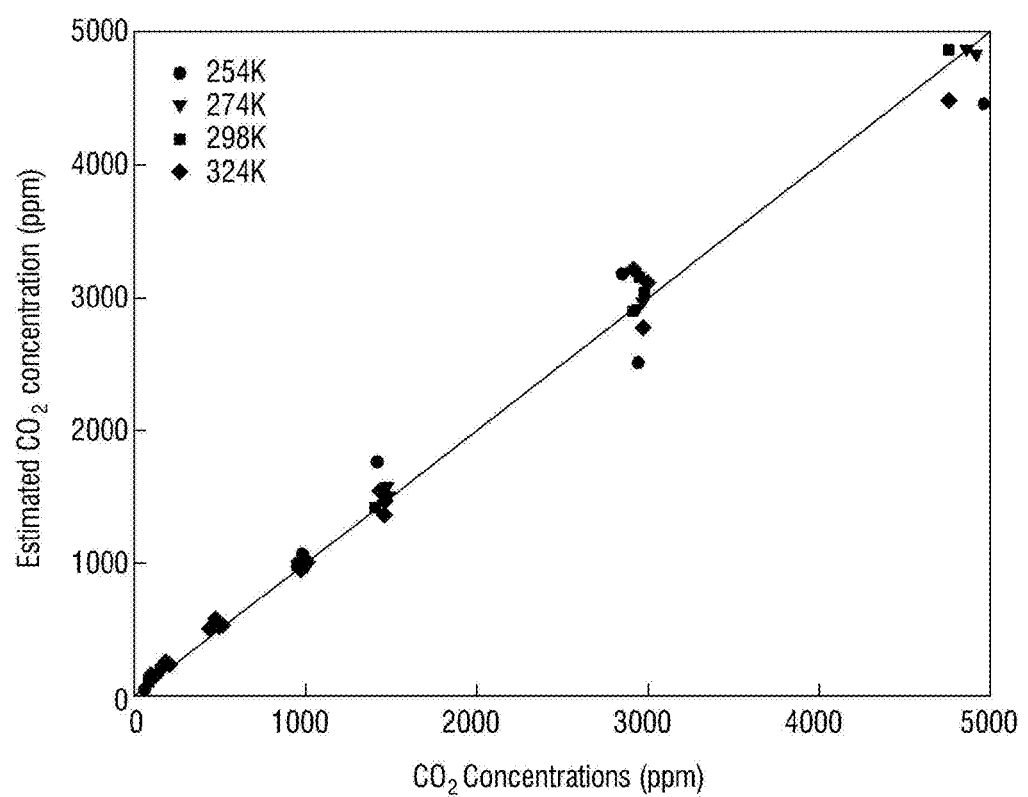
FIG. 16B is a graph drawing an estimated concentration of carbon dioxide using a gas sensor having a general reflector.

Herein, $V_{out}$ represents an output voltage of the detector, $V_{band}$ represents a voltage indicating an infrared energy density other than an absorption wavelength of target gas (e.g., carbon dioxide), $V_{gas}$ represents a voltage indicating an infrared energy density absorbed by the target gas, T represents a temperature, and k represents the product of the optical path and the absorption coefficient. First, according to an exemplary embodiment of the present disclosure, the gas sensor 100 deposited with the hydrophobic thin film (e.g., parylene-C) has an error of 10% or more at initial 100 ppm or less, but has an error within ±5% on average as the concentration increases. However, as illustrated in FIG. 16B, the gas sensor using the general reflector has an error of 20% or more at 100 ppm or less and has an average error of 15% or more at the entire concentration period, and the temperature compensation is not properly performed.

Therefore, a gas sensor that detects a specific gas using the same structure is fabricated to perform more accurately and reliably the function and the correction when depositing the hydrophobic thin film (e.g., parylene-C) on the surface of the reflector in the process for estimating the gas concentration and prevent corrosion of the reflector and dew formation of steam.

Further, in the present disclosure, the length of the optical path is effectively lengthened, thereby improving the high sensitivity of the sensor or the light intensity. In addition, the heater is disposed around the reflector to increase the temperature compared to the ambient temperature and prevent a decrease in the output voltage or a separate correction due to condensation of steam in the reflector. In addition, because of the hydrophobic thin film, the inner reflector has a function to prevent corrosion against corrosive gas. As a result of the experiment, it is possible to fabricate a structure having a remarkable difference (over 10%) from the existing structure.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. Therefore, it should be understood that the above-described exemplary embodiments are illustrative in all aspects and do not limit the present disclosure. The protective scope of the present disclosure should be construed based on the following claims, and all the technical concepts in the equivalent scope thereof should be construed as falling within the scope of the present disclosure.

What is claimed is:

1. A non-dispersive infrared carbon dioxide gas sensor deposited with a hydrophobic thin film, wherein
in the carbon dioxide gas sensor for measuring a concentration of carbon dioxide included in gas, the gas sensor is a white-cell,
in the white-cell, first and second reflectors are disposed to face a third reflector,
a light source is provided at one side of the third reflector and a first detector and a second detector are provided at another side of the third reflector, and
at least a part of a reflection surface of each of the first, second, and third reflectors is deposited with the hydrophobic thin film.

2. The non-dispersive infrared carbon dioxide gas sensor of claim 1, wherein a first hydrophobic thin film is deposited on the entire reflection surface of the first reflector, a second hydrophobic thin film is deposited on the entire reflection surface of the second reflector, and a third hydrophobic thin film is deposited on the entire reflection surface of the third reflector.

3. The non-dispersive infrared carbon dioxide gas sensor of claim 1, wherein the hydrophobic thin film includes one of parylene, OTS, and fluorine silane.

4. The non-dispersive infrared carbon dioxide gas sensor of claim 3, wherein the hydrophobic thin film includes parylene-C.

5. The non-dispersive infrared carbon dioxide gas sensor of claim 4, wherein a deposition thickness of the parylene-C is 0.2 μm to 0.7 μm.

6. The non-dispersive infrared carbon dioxide gas sensor of claim 4, wherein a deposition thickness of the parylene-C is 0.5 μm.

7. The non-dispersive infrared carbon dioxide gas sensor of claim 1, wherein the second detector is a reference detector and a Fresnel lens is further provided in front of the first detector.

8. The non-dispersive infrared carbon dioxide gas sensor of claim 1, wherein the second detector is a reference detector and a protective window and a hollow disk are further provided in front of the second detector.

9. The non-dispersive infrared carbon dioxide gas sensor of claim 1, wherein a protective window is further provided in front of the light source.

10. The non-dispersive infrared carbon dioxide gas sensor of claim 1, wherein a heater is further mounted in a vicinity of the first, second, and third reflectors.

11. The non-dispersive infrared carbon dioxide gas sensor of claim 10, wherein the heater comprises a first heater mounted in the vicinity of the third reflector and a second heater mounted in the vicinity of the first and second reflectors.

* * * * *